United States Patent [19]
Fellows

[11] Patent Number: 6,132,454
[45] Date of Patent: Oct. 17, 2000

[54] HEAT PACK

[75] Inventor: Adrian Neville Fellows, Hebden Bridge, United Kingdom

[73] Assignee: Hotties Thermal Packs Limited, London, United Kingdom

[21] Appl. No.: 09/171,356

[22] PCT Filed: Apr. 23, 1997

[86] PCT No.: PCT/GB97/01118

§ 371 Date: Oct. 16, 1998

§ 102(e) Date: Oct. 16, 1998

[87] PCT Pub. No.: WO97/41814

PCT Pub. Date: Nov. 13, 1997

[30] Foreign Application Priority Data

May 3, 1996 [GB] United Kingdom .................. 9609300

[51] Int. Cl.⁷ ........................................... A61F 7/00
[52] U.S. Cl. ............................................. 607/96; 607/108
[58] Field of Search ............................. 607/96, 108, 109, 607/110, 111; 383/901; 165/46

[56] References Cited

U.S. PATENT DOCUMENTS

| | | | |
|---|---|---|---|
| 4,376,437 | 3/1983 | Sundheim et al. | 602/2 |
| 4,488,552 | 12/1984 | McCann et al. | 607/112 |
| 5,088,487 | 2/1992 | Turner | 607/108 |
| 5,456,701 | 10/1995 | Stout | 607/104 |

*Primary Examiner*—Linda C. M. Dvorak
*Assistant Examiner*—R. Kearney
*Attorney, Agent, or Firm*—Harrison & Egbert

[57] ABSTRACT

A heat pack capable of being heated to at least 55° C. is provided and includes a flexible impervious outer container capable of being sealed to retain a liquid such as water therein and of maintaining its sealed integrity when heated to at least the aforesaid temperature. A porous, non-rigid filing material, which can absorb at least its own weight of the liquid, is located in the container. Advantageously, the pack contains a weight of liquid in the range 250 goods to 1250 goods, which liquid is water or compounds having one or more hydroxyl groups, or a mixture of water and such hydroxyl group compounds. In order to prevent microbial growth within the liquid-filled, sealed container, a predetermined quantity of a preservative at an appropriate concentration is also added to the fill. The filling material is preferably either fibrous or spongy in nature and advantageously may be a textile material or paper which is either recycled or would otherwise be treated as scrap or waste. Preferably also, air is removed from the outer container prior to it being sealed. The pack is also capable of use as a negative heat pack, i.e. a cool pack.

19 Claims, No Drawings

HEAT PACK

TECHNICAL FIELD

The present invention relates to a heat pack and in particular but not exclusively to a heat pack for therapeutic use. The pack could, however, be used for the application of heat in any suitable situation to both live and inanimate subjects. The pack is also capable of use as a negative heat pack, ie a cool pack, to abstract heat from live and inanimate subjects to which it is applied.

BACKGROUND ART

A conventional heat pack used for therapeutic use is a hot water bottle. While modern hot water bottles, which are made of rubber, are flexible they have the major disadvantage that they must be filled with hot water, which is usually at a temperature at or nearing boiling point. This is dangerous, particularly for children, the elderly, and persons with impaired movement or vision.

To overcome the aforementioned disadvantage, gel packs have been developed which can be heated, typically in a microwave oven, and used therapeutically. However, these tend to be expensive and hazardous in the case of a leak.

U.S. Pat. No. 4,765,338 discloses a heating or cooling pack for the entire scalp. The pack has been particularly developed for use as a cooling pack by patients undergoing chemotherapy treatment and has not been designed primarily as a heat pack, unlike the present invention.

U.S. Pat. No. 5,447,532 describes a water pillow or "ice bag" which comprises a closed bag made of a cloth or nonwoven fabric that has a high water permeability and that contains a water absorptive high polymer material, i.e. a gelling material. This pack has again been designed for use primarily as a cool pack.

Other conventional heat packs comprise electric blankets and pads, and devices using exothermic chemical and physical reactions. These types of apparatus tend to to be expensive to produce and/or to operate. In addition, those dependent on exothermic reactions can be unreliable and may not be sufficiently flexible in their heat-producing state to be able to mould themselves to a part of the body to be treated.

Variations on all these products have also been produced for use on inanimate objects but usually exhibit the same disadvantages as aforesaid.

The object of the present invention is to provide a heat pack which overcomes or substantially mitigates the aforementioned disadvantages and which is inexpensive and safe to use.

According to the present invention there is provided a heat pack for being heated to at least 55° C. and comprising a flexible, impervious outer container which is adapted to be sealed to retain a liquid therein and of maintaining its sealed integrity when heated to at least 55° .C and which contains a porous, non-rigid filling material and a predetermined quantity of a preservative at a concentration that inhibits microbial growth within the liquid-filled container when sealed, and characterised in that the filling material comprises at least one of a woven textile material, a nonwoven fabric, a sponge-like material, and paper, which filling material absorbs at least its own weight of said liquid.

For convenience and safety, the liquid used in the heat pack may be water. It will be appreciated, however, that the heat pack if not already supplied to the end-user in a water-filled, sealed condition, can be filled with cold water and sealed before being heated. The liquid within the container is absorbed by the porous filling material, which in addition to imparting a degree of rigidity to the heat pack is advantageous from a safety point of view after the heat pack has been heated should the outer container be ruptured.

The container may comprise a resealable bag or a sealed bag with a valve permitting it to be emptied, filled or topped up with liquid as desired.

It will be appreciated that when the pack is heated any air trapped inside the pack will expand. In extreme circumstances this can exacerbate expansion of the pack causing rupture. Hence, preferably, air is removed from the outer container prior to it being sealed. Advantageously, therefore, the valve permits air to be removed from the container after it has been filled with the liquid.

Alternatively, the container may be permanently sealed after the addition of water or other liquid and the removal of air therefrom, and may be supplied to the end user ready for use in this condition.

DETAILED DESCRIPTION OF THE INVENTION

More specifically, therefore, according to the present invention there is provided a heat pack for being heated to at least 55° C. and comprising a flexible, waterproof outer container which has been sealed after having had air removed therefrom to maintain its sealed integrity when heated to at least 55° C. and which contains a porous, non-rigid filling material, a liquid and a predetermined quantity of a preservative at a concentration that inhibits microbial growth within the sealed container, and characterised in that the filling material comprises at least one of a woven textile material, a nonwoven fabric, a sponge-like material, and paper in combination with at least the filling material's own weight of liquid which is absorbed by said filling material.

The air can be removed from the outer container by any suitable means such as pressing, suction, or vacuum sealing. Preferably, however, the outer container is vacuum sealed.

It has been found that in order to ensure that there is no excessive expansion of the pack during its heating to temperatures suitable for its application to parts of the human or animal body, the outer container is preferably exhausted of air down to a pressure equal to 100 millibars or less.

Removal of air from the outer container also imparts degree of rigidity to the pack which will thereby retain its shape during and after heating. This can be advantageous if the pack is to be made in a specific shape, for example for use with a particular area of the body or in the form of a toy for a child.

Heating of the pack is preferably accomplished using a microwave oven although other conventional heating methods could be used and would be required if the container were to be made of a metallized material. Such an alternative heating method could comprise immersion of the pack in hot water for a time sufficient to heat the pack through. Preferably, therefore, the pack is capable of being immersed in water which is at or near boiling point.

Another cause of potentially deleterious expansion of the pack arises if any water contained therein is vaporized during heating of the pack. Although in most embodiments of the invention and in most applications it will not be desirable to heat the pack to temperatures around or in excess of 100° C., if the pack is heated in a microwave oven the heating is not uniform so that while, for example, the mean temperature may be only 75° C. there may be hot spots with temperatures in excess of 100° C. The universal gas equation states that one gram mole of a substance changing from liquid phase to gas phase will occupy 22.4 liters of volume at normal temperature and pressure. Hence, 18 g of water, i.e. 18 ml of water, would occupy 22.4 liters when boiled and changed into water vapor. Hence, it will be appreciated that the vaporization of even a small percentage of the contents of a pack containing 500 g of water could give rise to a damaging expansion of the product.

In view of the foregoing, it is advantageous in some embodiments of the invention for at least a proportion of the water, and in some cases all of the water, to be replaced by a substance capable of being heated by a microwave oven but with a boiling point significantly higher than water. Suitable substances for this purpose preferably comprise compounds comprising one or more hydroxyl groups. For example, such substances may comprise one or more of glycerol, sorbitol or other polyhydric alcohols; ethylene glycol, propylene glycol or other glycols; glucose or other sugars; or any of a wide range of hydroxyl group containing compounds.

It is expected that in cases where a proportion of the water in the pack is replaced by hydroxl group containing compounds that at least one part hydroxyl group compound will be used to four parts water. In one preferred embodiment the pack comprises at least three parts hydroxyl group compound to two parts water.

It will be appreciated that the quantity of liquid within the pack will determine how quickly it can be heated for any given heating method. However, too little liquid within the pack will cause it to heat too rapidly, which can be dangerous, particularly if the pack is heated by a microwave oven. However, too much liquid is disadvantageous as the heating time is inconveniently protracted. Preferably, therefore, the quantity of liquid the pack contains is carefully predetermined. Advantageously, the pack contains a weight of liquid in the range 250 g to 1250 g. Optimally, however, from the point of view of user safety, convenience, heat content and weight, the pack contains a weight of liquid in the range 500 g to 1000 g.

Preferably, the container comprises a bag made from a substantially plastics material. Such a plastics material may comprise one of a polymer film, polymer laminate, co-extrusion, metallized plastics film, metallized plastics laminate, and an impervious heat-sealable polymeric nonwoven.

While the heat pack of the invention can be made inexpensively so that it could be disposed of after a single use, it is preferably made from materials which permit it to be heated and cooled, and therefore, used many times.

Preferably, therefore, the plastics material comprises at least one of polypropylene, polyethylene, a polyamide, polyvinyl chloride, an aramid polymer, a polyester. It may also comprise a combination of these plastics materials with at least one of a textile material, such as a textile scrim, a knitted or nonwoven fabric, a metal foil, and a metallized film, as a laminate.

Such materials are also conducive to the production of a container in the form of a bag which could be manufactured by heat sealing or high frequency welding the edges of sheets of such materials together. Alternatively, sheets extruded as a lay-flat tube can also be cut and sealed to form a bag. A resealable container could be produced similarly but with an opening to which a conventional water-tight closure means is attached.

The porous textile or paper filling material is preferably either fibrous or spongy in nature. Conveniently, such material may comprise scrap, waste or recycled textile or paper materials such as off-cuts and edge trim from other processes. In this way, the invention provides a convenient and beneficial means of using material which would otherwise comprise a troublesome and potentially environmentally damaging waste product.

The filling material may be used in the form of strips, swatches, rolls, and shreds, or may be specifically shaped, formed or cut.

Preferably, the filling material can absorb at least four times its own weight of liquid. In most cases it is expected that the filling material will be able to absorb between five and eight times its own weight of liquid and that it will be this quantity of liquid which will be used in the heat pack.

Additional filling materials may also be used in certain embodiments of the invention to produce a heat pack with certain properties, for example one with a greater or lesser rigidity or one which will hold its shape after being moulded following heating. Such additional filling materials may comprise any of expanded plastics materials, glass fibers, glass wool, ceramic fibers, and non-absorbent fabrics.

The fill for the container may also be modified by the addition of material containing superabsorbent polymers or other chemical absorbents either in combination with solid filling material, for example in a laminate form therewith, or by the direct addition of such chemicals. It may also be beneficial in some embodiments to add a viscosity modifier, for example a gum, modified cellulose, bentonite, hectorite, polyvinyl alcohol, or similar material to any of these.

Colorings, fragrances, pearlizing agents or other effect chemicals may also be added to the fill as required.

It is necessary to include in the heat pack a preservative to inhibit microbial activity such as fungal and bacterial growth which would detrimentally affect the pack once it had been first filled with water. Such growth would reduce the shelf life of a pack to the extent of rendering it uncommercial and, once present, may present a health hazard to the user.

Preferably, the preservative used in the heat pack comprises at least one of sorbic acid, citric acid, propionic acid, chlorhexidine, chlorbutol, bronopol, phenoxyethanol, phenyl ethyl alcohol, an ester of para hydroxybenzoic acid, 2.4 dichlorobenzyl alcohol, polyhexanide, a phenolic compound, and a quaternary ammonium compound.

Such preservatives are known for their particular suitability for use in consumer products such as foodstuffs and cosmetics because they are safe to use and are stable enabling the resulting product to exhibit a long-term integrity. However, any suitable preservative could be used.

It will be appreciated that the concentration of preservative required and the nature of the preservative will depend on its own nature, the nature of the filling material and the container, and on the desired life of the heat pack itself.

While fabrics and textile materials which have been pre-treated with biocidal compositions could be used as filling materials for the pack, the use of such filling materials would increase the cost of the heat pack and the invention is not, therefore, limited to their use.

Six examples of heat packs according to the present invention will now be described.

EXAMPLE 1

Outer Container 50 micron polypropylene sheets cut to size and rotary heat sealed to form a bag
Fill Thermally bonded viscose and cotton nonwoven fabric, wetted with 500 g water containing a preservative of 0.2% methyl para hydroxybenzoate and 0.04% propyl para hydroxybenzoate.

EXAMPLE 2

Outer Container A resealable laminate pouch
Fill A cotton fiber, cotton towelling wetted with water containing a preservative of 500 ppm benzalkonium chloride and 500 ppm polyhexanide.

EXAMPLE 3

Outer Container A nylon and polythene co-extrusion pouch capable of retaining 500 ml of liquid
Fill 100 g of viscose nonwoven fabric wetted with 200 ml of water and 300 ml of glycerol containing a preservative of 500 ppm benzalkonium chloride and 500 ppm polyhexanide.

EXAMPLE 4

Outer Container A nylon and polythene laminate pouch capable of retaining 630 ml of liquid
Fill 120 g of viscose nonwoven fabric wetted with 630 ml of water containing a preservative of 500 ppm benzalkonium chloride and 500 ppm polyhexanide.

EXAMPLE 5

Outer Container A high frequency welded polyvinyl chloride bag.
Fill A wet laid viscose and wood pulp cellulose nonwoven fabric and airlaid paper mix wetted with water containing a preservative of 0.5% chlorbutol and 0.5% phenyl ethyl alcohol.

EXAMPLE 6

Outer Container A high frequency welded polyvinyl chloride bag.
Fill A wet laid viscose and wood pulp cellulose nonwoven fabric wetted with glycerol containing a preservative of 0.5% chlorbutol and 0.5% phenyl ethyl alcohol.

Thus the invention provides a heat pack which is capable of being heated to a temperature of at least 55° C.; which is able to withstand conventional readily available heating methods, such as the use of microwaves; and which is relatively inexpensive and safe to use.

The internal structure of the pack may also be modified as desired by the addition of physical or chemical agents to alter its bulk or rheological properties. In addition, the external appearance, tactile properties, heat transference, and function of the pack may be modified by the use of fixed or loose coverings.

As previously mentioned, it will be appreciated that in most embodiments detailed above the pack is also capable of use as a negative heat pack, ie. a cool pack, which can be used to abstract heat from live and inanimate subjects to which it is applied. In this case the pack would be cooled, conveniently by being placed in a refrigerator or freezer for a predetermined period, before use in the same manner as the heat pack described heretofore. References herein, in both the description and the claims to the term "heat pack" are therefore to be understood in this light.

What is claimed is:

1. A heat pack comprising:
    a sealed flexible impervious container capable of retaining a liquid therein, said container capable of remaining sealed when heated to a temperature of at least 55° C.;
    a porous non-rigid filling material located within said container, said filling material selected from the group consisting of at least one of a woven textile material, a nonwoven material, a sponge-like material, and a paper material, said filling material capable of absorbing liquid in an amount at least equal in weight to a weight of said filling material;
    a preservative having a concentration which inhibits microbial growth interior of said container; and
    a valve means positioned within said container for permitting said container to be emptied of liquid and filled with liquid, said valve means for removing a gas from said container after said container has been filled with the liquid, said gas selected from the group consisting of at least one of air and steam.

2. A heat pack as claimed in claim 1, wherein the container comprises a resealable bag.

3. A heat pack as claimed in claim 1 wherein said filling material absorbs said liquid in an amount at least four times said weight of said filling material.

4. A heat pack as claimed in claim 1 wherein said preservative is selected from the group consisting of at least one of sorbic acid, citric acid, propionic acid, chlorhexidine, chlorbutol, bronopol, phenoxyethanol, phenyl ethyl alcohol, an ester of parahydroxybenzoic acid, 2.4 dichlorobenzyl alcohol, polyhexanide, a phenolic compound, and a quaternary ammonium compound.

5. A heat pack as claimed in claim 1, said container capable of remaining related at a temperature of at least a boiling point of water.

6. A heat pack suitable for being heated to a temperature of at least 55° C., the heat pack comprising:
    a vacuum-sealed flexible waterproof container capable of retaining a liquid therein, said container capable of maintaining a sealed integrity thereof when heated to at least 55° C., said container having an internal pressure which is reduced by removal of air therefrom during a sealing of said container; and
    a porous non-rigid filling material received within said container, said filling material selected from the group consisting of at least one of a woven textile material, a nonwoven fabric, a sponge-like material and a paper material, said filling material absorbing said liquid in an amount equal to at least a total weight of said filling material, said liquid comprising a preservative in a concentration which inhibits microbial growth within said container.

7. A heat pack as claimed in claim 6 wherein said container has been exhausted of air down to a pressure equal to 100 millibars or less.

8. A heat pack as claimed claim 7 wherein the liquid comprises at least one of water and compounds comprising one or more hydroxyl groups.

9. A heat pack as claimed claim 6 wherein the liquid comprises a mixture of water and compounds comprising one or more hydroxyl groups in the proportion of at least 1 part hydroxyl group compound to 4 parts water upwards towards total replacement of the water.

10. A heat pack as claimed in claim 6 wherein the liquid is selected from the group consisting of at least one of water, glycerol, sorbitol, polyhydric alcohols, ethylene glycol, propylene glycol, and glucose.

11. A heat pack as claimed in claim 6 wherein said container contains a weight of liquid between 250 g to 1250 g.

12. A heat pack as claimed in claim 6 wherein said container contains a weight of liquid between 500 g to 1000 g.

13. A heat pack as claimed in claim 6 wherein said the container comprises a bag made from a polymeric material.

14. A heat pack as claimed in claim 13, wherein said polymeric material is selected from the group consisting of a polymer film, a polymer laminate, a co-extruded metallized polymeric film, a metallized polymeric laminate and an impervious heat-sealable nonwoven polymer.

15. A heat pack as claimed in claim 13 wherein said polymeric material is selected from the group consisting of at least one of polyethylene, polypropylene, a polyamide, polyvinyl chloride, an aramid polymer and a polyester.

16. A heat pack as claimed in claim 13 wherein said polymeric material comprises a polymer laminated with another material said polymer selected from the group consisting of at least one of polyethylene, polypropylene, a polyamide, polyvinyl chloride, an aramid polymer and a polyester, said another material selected from the group consisting of at least one of a textile material, a metal foil and a metallized film.

17. A heat pack as claimed claim 6 wherein said filling material absorbs said liquid in an amount at least four times said weight of said filling material.

18. A heat pack as claimed in claim 6 wherein said preservative is selected from the group consisting of at least one of sorbic acid, citric acid, propionic acid, chlorhexidine, chlorbutol, bronopol, phenoxyethanol, phenyl ethyl alcohol, an ester of para hydroxybenzoic acid, 2.4 dichlorobenzyl alcohol, polyhexanide, a phenolic compound, and a quaternary ammonium compound.

19. A heat pack as claimed in claim 6 wherein said liquid has a component selected from the group consisting of gum, cellulose, bentonite, hectorite and polyvinyl alcohol.

\* \* \* \* \*